United States Patent

Sevrin et al.

Patent Number: 5,418,248
Date of Patent: May 23, 1995

[54] 2-THIENYLIMIDAZO[2,1-β]BENZO-THIAZOLE-3-ACETIC ACID DERIVATIVES, THEIR PREPARATION AND THEIR USE

[75] Inventors: Mireille Sevrin, Paris; Claude Morel, Magny les Hameaux; Michel Mangane, Châtillon S/Bagneux; Pascal George, ST Arnoult en Yvelines, all of France

[73] Assignee: Synthelabo, Le Plessis Robinson, France

[21] Appl. No.: 175,249

[22] Filed: Dec. 29, 1993

[30] Foreign Application Priority Data

Dec. 30, 1992 [FR] France .................. 92 15889

[51] Int. Cl.⁶ .............. C07D 513/04; A61K 31/425
[52] U.S. Cl. ........................ 514/366; 548/151
[58] Field of Search ................ 548/151; 514/366

[56] References Cited

U.S. PATENT DOCUMENTS 4,896,863 1/1990 Hedgecock et al. ............ 514/366

FOREIGN PATENT DOCUMENTS 524055 1/1993 European Pat. Off. .......... 548/151

OTHER PUBLICATIONS

A. N. El Shorbagi et al., Chemical and Pharmaceutical Bulletin, vol. 36, No. 12, 1988, pp. 4760–4768.

*Primary Examiner*—Robert Gerstl
*Attorney, Agent, or Firm*—Jacobson, Price, Holman & Stern

[57] ABSTRACT

Compounds of the formula:

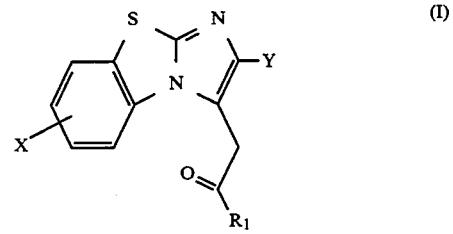

in which $R_1$ represents a hydroxy group, a $C_1$–$C_4$ alkoxy group or an amino group of general formula —$NR_4R_5$ in which $R_4$ and $R_5$ each represent, independently of each other, a hydrogen atom, a straight or branched $C_1$–$C_4$ alkyl group, an allyl group or a methoxyethyl group, or alternatively —$NR_4R_5$ represents a heterocycle containing 3 to 6 carbon atoms, Y represents a thienyl group optionally substituted by an alkyl group, and X represents a hydrogen or halogen atom, are useful as anticonvulsants and auxiolytics.

4 Claims, No Drawings

2-THIENYLIMIDAZO[2,1-β]BENZOTHIAZOLE-3-ACETIC ACID DERIVATIVES, THEIR PREPARATION AND THEIR USE

The present invention provides novel 2-thienylimidazo[2,1-b]benzothiazole-3-acetic acid derivatives, having therapeutic utility.

The compounds of the invention have the formula:

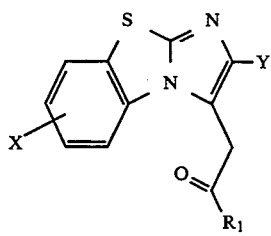
(I)

in which

R$_1$ represents a hydroxy group, a C$_1$–C$_4$ alkoxy group or an amino group of formula —NR$_4$R$_5$ in which R$_4$ and R$_5$ each represent, independently of each other, a hydrogen atom, a straight or branched C$_1$–C$_4$ alkyl group, an allyl group or a methoxyethyl group, or alternatively —NR$_4$R$_5$ represents a heterocycle containing 3 to 6 carbon atoms, X represents a hydrogenor halogen atom, and Y represents a thienyl group of formula (IA) or (IB)

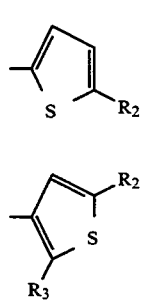

in which R$_2$ and R$_3$ each represent, independently of each other, a straight or branched C$_1$–C$_4$ alkyl group.

The compounds of the invention can exist in the form of free bases or acid addition salts.

R$_1$ preferably represents a methylamino group. X is preferably hydrogen. In formula IA, R$_2$ is preferably methyl. In formula IB, R$_2$ and R$_3$ are preferably both methyl.

In accordance with a feature of the invention, these compounds are prepared by the process illustrated by the scheme below.

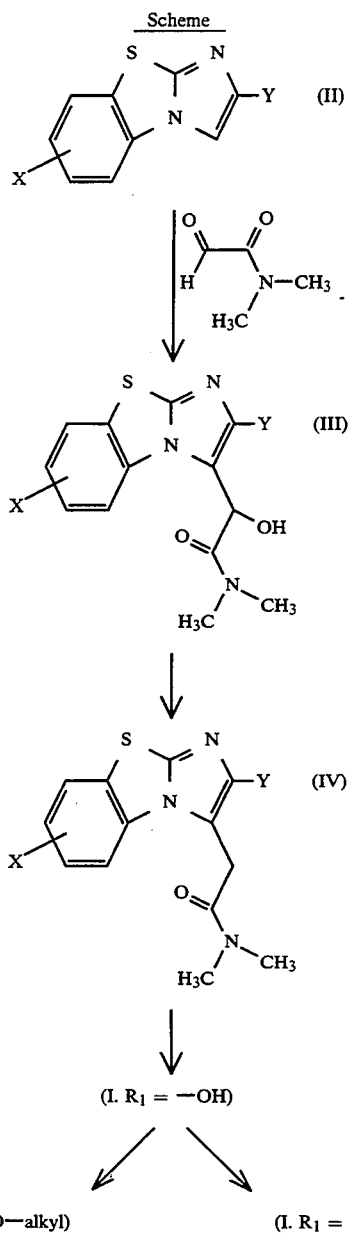

A 2-thienylimidazo[2,1-b]benzothiazole of formula (II), in which X and Y are as defined above, is reacted with N,N-dimethylglyoxamide (which is prepared in situ from 2,2-diethoxy-N,N-dimethylacetamide, as described in European Application EP-251859) in a protic solvent such as acetic acid, at a temperature of 20° to 80° C.

The α-hydroxyacetamide derivative of formula (III) is then treated with a polyhalide of sulphuric or phosphoric acid, for example thionyl chloride or phosphorus oxychloride, or an equivalent reagent, in an inert solvent, for example a chlorine-containing or ethereal solvent such as dichloromethane or tetrahydrofuran, at a temperature of 20° to 80° C., to form the corresponding α-haloacetamide derivative. The latter is then reacted either with a reducing agent such as a simple or complex alkali metal hydride, for example sodium or potassium borohydride, in a protic solvent, for example an aliphatic alcohol such an methanol or ethanol, or in a water-miscible inert solvent, for example dioxane or tetrahydrofuran, at a temperature of −40° to 40° C., or with a reducing agent such as an alkali metal hyposulphite or dithionite, for example sodium hyposulphite or dithionite, or alternatively with sodium hydroxymethylsulphoxylate (Rongalite ®), in an inert solvent, for example a chlorine-containing solvent such as dichloromethane, optionally in the presence of a water-miscible inert cosolvent, for example N,N-dimethylformamide or N-methylpyrrolidone, at a temperature of 20° to 40° C.

A 2-thienylimidazo[2,1-b]benzothiazole-3-acetamide of general formula (IV) is thus obtained which corresponds to the formula (I) when $R_1$ represents a group of formula $-N(CH_3)_2$.

If desired, this compound is converted to the acid of formula (I) in which $R_1$ represents a hydroxy group, by hydrolysis with a strong base, for example sodium hydroxide, in a protic solvent, for example 2-methoxyethanol, in the presence of water.

If it is desired to prepare a compound of formula (I) in which $R_1$ represents a group of formula $-NR_4R_5$ other than a group of formula $-N(CH_3)_2$, the acid of formula (I, $R_1=OH$) is reacted with N,N'-carbonyldiimidazole, in an inert solvent, for example a chlorine-containing or ethereal solvent such as dichloromethane or tetrahydrofuran, at a temperature of 20° to 50° C., in order to obtain the corresponding imidazolide, and finally, the latter is treated with an amine of formula $HNR_4R_5$ (in which $R_4$ and $R_5$ are as defined above) at a temperature of 0° to 25° C.

Finally, if desired, the acid of formula (I, $R_1=OH$) can be converted into an ester (I, $R_1=-O-$alkyl) by known methods.

The starting 2-thienylimidazo[2,1-b]benzothiazoles of general formula (II) can be prepared by methods similar to that described in *Khim. Geterotsikl. Soedin.*, 9, 1271–1274 (1972).

The Examples below illustrate the preparation of some compounds of the invention. Elemental microanalyses and the I.R. and N.M.R. spectra confirm the structures of the compounds obtained. The numbers indicated in brackets in the titles of the examples correspond to those of the 1st column of the table given later.

EXAMPLE 1

(Compound No.5)

N,N-Dimethyl-2-(5-methylthien-2-yl)imidazo[2,1-b]-benzothiazole-3-acetamide.

1.1. α-Hydroxy-N,N-Dimethyl-2-(5-methylthien-2-yl)imidazo[2,1-b]benzothiazole-3-acetamide.

30 g (0.171 mole) of 2,2-diethoxy-N,N-dimethylacetamide and 460 ml of acetic acid are mixed in a 1000 ml round-bottomed flask, the solution is heated to 45°–50° C. and 4.6 ml of 36% hydrochloric acid (that is to say 1.65 g or 0.045. equivalent) are added dropwise. The mixture is stirred for 1 h at 45°–50° C. 14 g (0.171 mole) of sodium acetate are then added, the mixture is stirred for 15 minutes at 45°–50° C. and then, in a single portion, 15.4 g (0.057 mole) of 2-(5-methylthien-2-yl)imidazo[2,1-b]benzothiazole are added and the mixture is heated, with stirring, at 50°–55° C. for 3 h. The solvent is evaporated under reduced pressure, the solid is taken up in water and dichloromethane, a residue is separated by filtration, the organic phase is separated, it is washed with a solution of sodium bicarbonate and it is dried over sodium sulphate. The solvent is evaporated under reduced pressure and the residue is purified by chromatography on a silica gel column, eluting with a 98/2 mixture of dichloromethane/methanol. 15.6 g of compound are obtained which are used as such in the next stage.

1.2. α-Chloro-N,N-dimethyl-2-(5-methylthien-2-yl)imidazo[2,1-b]benzothiazole-3-acetamide hydrochloride.

15.6 g (0.0474 mole) of α-hydroxy-N,N-dimethyl-2-(5-methylthien-2-yl)imidazo[2,1-b]benzothiazole-3-acetamide are treated with 34.8 ml (or 57.1 g, that is to say 0.48 mole) of thionyl chloride in 200 ml of dichloromethane. The mixture is refluxed for 5 h, the solvent and the excess thionyl chloride are evaporated under reduced pressure, and two entrainments are performed in toluene under reduced pressure. The solid obtained is isolated and it is dried under vacuum in the presence of potassium hydroxide pellets. 17.8 g of a chestnut coloured solid are obtained which are used as such in the next stage.

1.3. N,N-Dimethyl-2-(5-methylthien-2-yl)imidazo[2,1-b]benzothiazole-3-acetamide.

40 g (0.0938 mole) of α-chloro-N,N-dimethyl-2-(5-methylthien-2-yl)imidazo[2,1-b]benzothiazole-3-acetamide hydrochloride in solution in 1200 ml of dichloromethane are treated with 43.6 (0.283 mole) of Rongalite ®, while stirring the mixture at room temperature for 6 h. The suspension is filtered, it is rinsed with dichloromethane and the organic phase is washed (pH=1) with 500 ml of 0.5N sodium hydroxide up to a pH>10, then to neutral pH with a saturated sodium chloride solution. The organic phase is dried over sodium sulphate and the solvent is evaporated under reduced pressure. A beige-coloured solid is obtained which is purified by chromatography on a silica gel column, eluting with a 95/5 mixture of dichloromethane/methanol. 23.9 g of a white solid are obtained. Melting point: 216°–218° C.

EXAMPLE 2

(Compound No.11)

2-(5-methylthien-2-yl)imidazo[2,1-b]benzothiazole-3-acetic acid.

23.8 g (0.067 mole) of N,N-dimethyl-2-(5-methylthien-2-yl) imidazo[2,1-b]benzothiazole-3-acetamide and 450 ml of 2-methoxyethanol are introduced into a 1 liter round-bottomed flask, and the mixture is stirred and it is heated on an oil bath at around 130° C. until the solid dissolves. A solution of 13.4 g (0.335 mole) of sodium hydroxide pellets in 70 ml of water is added hot, with precaution, then after 30 minutes, a further 13.4 g (0.335 mole) of sodium hydroxide pellets in 70 ml of water, and the heating is maintained for 7 h 30 min, while monitoring the progress of the reaction by thin-layer chromatography. The mixture is cooled to around 20° C., the solvent is evaporated under reduced pressure, without exceeding 60° C. 1200 ml of water are added to the residue, an insoluble matter is removed by filtration, 150 ml of acetic acid are added to the filtrate up to a pH=4. A yellow-coloured precipitate is obtained which is stirred for 30 minutes while cooling to around 5° C. The solid is separated by filtration, it is washed with water and then with diethyl ether, and it is dried under vacuum at around 60° C. 17.5 g of compound are obtained of which 1.65 g (0.005 mole) are purified by recrystallization from 250 ml of boiling methanol. 1.1.g of a light yellow-coloured solid are isolated. Melting point: 255°–259° C.

EXAMPLE 3

(Compound No.1)

2-(5-Methylthien-2-yl)imidazo[2,1-b]benzothiazole-3-acetamide.

1.6 g (0.005 mole) of 2-(5-methylthien-2-yl)imidazo[2,1-b]-benzothiazole-3-acetic acid are treated, at room temperature, with 0.85 g (0.005 mole) of N,N'-carbonyldiimidazole in 30 ml of anhydrous tetrahydrofuran for 3 h 30 min. The mixture is cooled using an ice bath, an excess of ammonia in 10 ml of anhydrous tetrahydrofuran cooled to $-10°$ C. is added, and the mixture is stirred for 4 h at room temperature. The solvent is evaporated under reduced pressure, the solid is collected by filtration, it is washed with water up to neutral pH, then with ethanol, and finally with ethyl ether. After recrystallization from methanol, 1 g of a beige compound is obtained. Melting point: 243°–245° C.

EXAMPLE 4

(Compound No.4)

2-(5-Methylthien-2-yl)-N-propylimidazo[2,1-b]-benzothiazole-3-acetamide.

1.6 g (0.005 mole) of 2-(5-methylthien-2-yl)imidazo[2,1-b]-benzothiazole-3-acetic acid are treated, at room temperature, with 0.85 g (0.005 mole) of N,N'-carbonyldiimidazole in 30 ml of anhydrous tetrahydrofuran for 3 h 30 min. A solution composed of 3 g (0.05 mole) of propylamine in 10 ml of anhydrous tetrahydrofuran is added and the mixture is stirred for 4 h at room temperature. The solvent is evaporated under reduced pressure, the compound is collected by filtration, it is washed with water up to neutral pH, then with ethanol and finally with ethyl ether and it is purified by recrystallization from methanol. 1.1 g of a light yellow solid are obtained. Melting point: 204°–206° C.

EXAMPLE 5

(Compound No.12)

Ethyl 2-(5-Methylthien-2-yl)imidazo[2,1-b]benzothiazole-3-acetate.

The ethyl ester is prepared from 1.65 g (0.005 mole) of 2-(5-methylthien-2-yl)imidazo[2,1-b]benzothiazole-3-acetic acid by refluxing for 6 h in ethanol in the presence of sulphuric acid. After chromatography on a silica gel column, eluting with a 95/5 mixture of dichloromethane/methanol, and after recrystallization from ethyl acetate, a beige-coloured solid is obtained. Melting point: 124°–126° C.

EXAMPLE 6

(Compound No.18)

N,N-Dimethyl-2-(2,5-dimethylthien-3-yl)imidazo[2,1-b]-benzothiazole-3-acetamide.

6.1. α-Hydroxy-N,N-dimethyl-2-(2,5-dimethylthien-3-yl)imidazo[2,1-b]benzothiazole-3-acetamide.

40.7 g (0,232 mole) of 2,2-diethoxy-N,N-dimethylacetamide and 630 ml of acetic acid are mixed in a 1000 ml round-bottomed flask, the solution is heated to 50° C., 6.3 ml (0.06 mole) of 36% hydrochloric acid are added dropwise and the stirring is continued at 50° C. for 1 h. 19 g (0.232 mole) of sodium acetate are then added, the mixture is stirred for 15 minutes, then 22 g (0.077 mole) of 2-(2,5-dimethylthien-3-yl)imidazo[2,1-b]benzothiazole are added in a single portion, and the heating is maintained at 50° C. for 6 h. The solvent is evaporated under reduced pressure and at a temperature of less than 50° C., the residue is taken up in dichloromethane and water, the pH is adjusted to 9 with ammonium hydroxide, the organic phase is separated, it is washed with water, it is dried over sodium sulphate and the solvent is evaporated under reduced pressure. 31 g of an oily product are obtained which are used as such in the next stage.

6.2. α-Chloro-N,N-dimethyl-2-(2,5-dimethylthien-3-yl)imidazo[2,1-b]benzothiazole-3-acetamide hydrochloride.

31 g (0.077 mole) of α-hydroxy-N,N-dimethyl-2-(2,5-dimethylthien-3-yl)imidazo[2,1-b]benzothiazole-3-acetamide, 150 ml of dichloromethane and 2 ml of N,N-dimethylformamide are introduced into a 500 ml round-bottomed flask, a solution of 58 ml (0.77 mole) of thionyl chloride in 100 ml of dichloromethane is added, and the mixture is refluxed for 6 h. The solvent and the excess thionyl chloride are evaporated under reduced pressure, two entrainments are performed with toluene under reduced pressure, the solvents are evaporated under high vacuum until a constant weight is obtained, and 34 g of an oil are obtained, which oil crystallizes.

6.3. N,N-Dimethyl-2-(2,5-dimethylthien-3-yl)imidazo[2,1-b]-benzothiazole-3-acetamide.

34 g (0.077 mole) of α-chloro-N,N-dimethyl-2-(2,5-dimethylthien-3-yl)imidazo[2,1-b]benzothiazole-3-acetamide hydrochloride in solution in 500 ml of dichloromethane are treated with 36.9 g (0.24 mole) of Rongalite®, while stirring the mixture at room temperature for 24 h. The organic phase is separated after settling has taken place, the solid residue is washed with dichloromethane, the organic phase is washed with a saturated sodium hydrogen carbonate solution and then with water, it is dried over sodium sulphate, the solvent is evaporated under reduced pressure and 22 g of solid are obtained. After recrystallization from ethanol and treatment with vegetable black, 17 g of pale yellow crystals are finally obtained. Melting point: 194°–195° C.

EXAMPLE 7

(Compound No.23)

2-(2,5-Dimethylthien-3-yl)imidazo[2,1-b]benzothiazole-3-acetic acid.

14 g (0.0379 mole) of N,N-dimethyl-2-(2,5-dimethylthien-3-yl)imidazo[2,1-b]benzothiazole-3-acetamide and 350 ml of 2-methoxyethanol are introduced into a 1000 ml round-bottomed flask, the solution is heated to 100° C., 25 ml of a solution at 30% sodium hydroxide (0.189 mole) are added, the mixture is heated at boiling temperature for 30 minutes, a further 25 ml of 30% sodium hydroxide are added and the heating is maintained for 4 h. 25 ml of a solution at 30% sodium hydroxide are again added and the mixture is heated for a further 3 h. The solvents are evaporated under reduced pressure, the residue is taken up in 500 ml of water, the insoluble matter is separated by filtration and the pH of the filtrate is adjusted to 4 with acetic acid. A yellow precipitate is obtained which is separated by filtration and it is washed with water and then with diethyl ether. After crystallization from methanol, 9 g of light yellow crystals are obtained. Melting point: 249°–250° C.

EXAMPLE 8

(Compound No.14)

2-(2,5-Dimethylthien-3-yl)-N-methylimidazo[2,1-b]-benzothiazole-3-acetamide.

A solution of 1.5 g (0.0044 mole) of 2-(2,5-dimethyl-thien-3-yl)imidazo[2,1-b]benzothiazole-3-acetic acid in 30 ml of anhydrous tetrahydrofuran is treated, at room temperature, with 0.85 g (0.005 mole) of N,N'-carbonyl-diimidazole for 30 minutes. The solution which has become clear is cooled to 0° C. and a stream of methylamine is passed through it for 30 minutes. The mixture is allowed to return to room temperature, the stirring is continued for 3 h, the solvent is evaporated under reduced pressure, the residue is taken up in 10 ml of water, it is extracted with dichloromethane, the organic phase is separated, it is washed with water, it is dried over sodium sulphate, the solvent is evaporated under reduced pressure, and the residue is crystallized from ethyl acetate. 1 g of pale yellow crystals is finally obtained. Melting point: 238°–239° C.

EXAMPLE 9

(Compound No.21)

6-Chloro-N,N-dimethyl-2-(2,5-dimethylthien-3-yl)imidazo[2,1-b]benzothiazole-3-acetamide.

9.1. 6-Chloro-α-hydroxy-N,N-dimethyl-2-(2,5-dimethylthien-3-yl)imidazo[2,1-b]benzothiazole-3-acetamide.

A mixture of 27 g (0.153 mole) of 2,2-diethoxy-N,N-dimethylacetamide, 4 ml (0.04 mole) of 36% hydrochloric acid and 200 ml of acetic acid are heated for 1 h at 45° C. 12.56 g (0.153 mole) of sodium acetate are added, the heating is continued for 15 minutes, 15 g (0.0479 mole) of 6-chloro-2-(2,5-dimethylthien-3-yl)imidazo[2,1-b]-benzothiazole are added and the mixture is heated at 50° C. for 6 h. The acetic acid is removed by distillation under reduced pressure, the residue is taken up in a mixture of water and dichloromethane, ammonium hydroxide is added, the organic phase is separated, it is washed, it is dried over sodium sulphate and the solvent is evaporated under reduced pressure. 18 g of an oily product are obtained, which product crystallizes.

9.2. 6-Chloro-N,N-dimethyl-2-(2,5-dimethylthien-3-yl)imidazo[2,1-b]benzothiazole-3-acetamide.

18 g (0.0431 mole) of 6-chloro-α-hydroxy-N,N-dimethyl-2-( 2,5-dimethylthien-3-yl)imidazo[2,1-b]benzothiazole-3-acetamide are treated with 31 ml (0.43 mole) of thionyl chloride, 2 ml of N,N-dimethyl formamide and 100 ml of dichloromethane at the reflux temperature for 6 h. The solvent and the excess thionyl chloride are removed under reduced pressure, the residue is taken up in diethyl ether, the solid is washed with diethyl ether and it is dried. 21 g of α,6-dichloro-N,N-dimethyl-2-(2,5-dimethylthien-3-yl)imidazo[2,1-b]benzothiazole-3-acetamide hydrochloride are obtained which are reduced with 21 g (0.136 mole) of Rongalite ® in 300 ml of dichloromethane at room temperature for 24 h. The solution is separated after settling has taken place, the solid is washed with dichloromethane, the organic phase is washed with a saturated sodium hydrogen carbonate solution and then with water, it is dried over sodium sulphate and the solvent is evaporated under reduced pressure. An oil is obtained which crystallizes and which is recrystallized from acetonitrile. 14.4 g of yellow needles are finally isolated. Melting point: 202°–203° C.

The Table below illustrates the chemical structures and the physical properties of some compounds according to the invention. All the compounds are in the form of bases.

TABLE

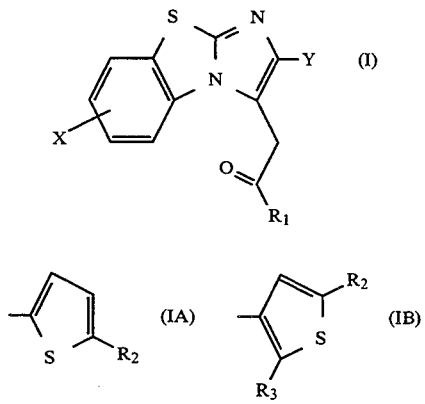

| No. | $R_1$ | Y | $R_2$ | $R_3$ | X | m.p. (°C.) |
|---|---|---|---|---|---|---|
| 1 | —$NH_2$ | IA | —$CH_3$ | — | H | 243–245 |
| 2 | —NH—$CH_3$ | IA | —$CH_3$ | — | H | 271–273 |
| 3 | —NH—$CH_2CH_3$ | IA | —$CH_3$ | — | H | 246–248 |
| 4 | —NH—$CH_2CH_2CH_3$ | IA | —$CH_3$ | — | H | 204–206 |
| 5 | —$N(CH_3)_2$ | IA | —$CH_3$ | — | H | 216–218 |
| 6 | —$N(CH_3)$—$CH_2CH_2CH_3$ | IA | —$CH_3$ | — | H | 154–156 |
| 7 | —$N(CH_3)$—$CH_2CH$=$CH_2$ | IA | —$CH_3$ | — | H | 146–148 |
| 8 | —$N(CH_2CH_3)$—$CH_2CH_2CH_3$ | IA | —$CH_3$ | — | H | 125–127 |
| 9 | —$N(CH_2CH_2CH_3)_2$ | IA | —$CH_3$ | — | H | 153–155 |

TABLE-continued

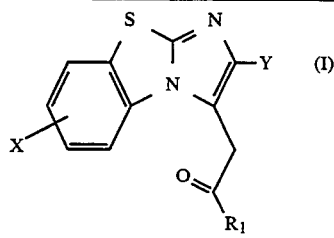

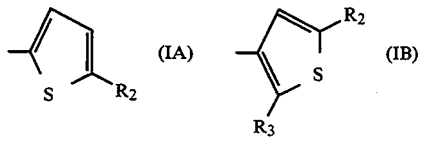

| No. | R₁ | Y | R₂ | R₃ | X | m.p. (°C.) |
|---|---|---|---|---|---|---|
| 10 | —N⟨pyrrolidine⟩ | IA | —CH₃ | — | H | 262–264 |
| 11 | —OH | IA | —CH₃ | — | H | 255–259 |
| 12 | —O—CH₂CH₃ | IA | —CH₃ | — | H | 124–126 |
| 13 | —NH₂ | IB | —CH₃ | —CH₃ | H | 258–259 |
| 14 | —NH—CH₃ | IB | —CH₃ | —CH₃ | H | 238–239 |
| 15 | —NH—CH₂CH₃ | IB | —CH₃ | —CH₃ | H | 162–163 |
| 16 | —NH—CH₂CH₂CH₃ | IB | —CH₃ | —CH₃ | H | 176–177 |
| 17 | —NH—CH₂CH₂—O—CH₃ | IB | —CH₃ | —CH₃ | H | 126–127 |
| 18 | —N(CH₃)₂ | IB | —CH₃ | —CH₃ | H | 194–195 |
| 19 | —NH—CH₃ | IB | —CH₃ | —CH₃ | 6-Cl | 233–234 |
| 20 | —NH—CH₂CH₂CH₃ | IB | —CH₃ | —CH₃ | 6-Cl | 217–218 |
| 21 | —N(CH₃)₂ | IB | —CH₃ | —CH₃ | 6-Cl | 202–203 |
| 22 | —N(CH₃)₂ | IB | —CH₃ | —CH₂CH₂CH₃ | H | 194–195 |
| 23 | —OH | IB | —CH₃ | —CH₃ | H | 249–250 |
| 24 | —OH | IB | —CH₃ | —CH₃ | 6-Cl | >260 |
| 25 | —N⟨pyrrolidine⟩ | IB | —CH₃ | —CH₃ | H | 175–176 |

The compounds of the invention have been subjected to pharmacological trials which have demonstrated their usefulness as substances with therapeutic activity.

Study of membrane binding with respect to the $\omega_1$ (type 1 benzodiazepines) and $\omega_2$ receptors (type 2 benzodiazepines).

The affinity of the compounds for the $\omega_1$ receptors of the cerebellum and the $\omega_2$ receptors of the spinal cord was determined according to a variant of the method described by S. Z. Langer and S. Arbilla in *Fund. Clin. Pharmacol.*, 2, 159–170 (1988), with the use of ³H-flumazenil instead of ³H-diazepam as radioligand. The cerebellum or spinal cord tissue is homogenized for 60 s in 120 or 30 volumes, respectively, of ice cold buffer (50 mM Tris/HCl, pH 7.4, 120 mM NaCl, 5 mM KCl) and then, after a 1/3 dilution, the suspension is incubated with ³H-flumazenil (specific activity 78 Ci/mmol, New England Nuclear) at a concentration of 1 nM and with the compounds of the invention at various concentrations, in a final volume of 525 μl. After incubating for 30 minutes at 0° C., the samples are filtered under vacuum on Whatman GF/B ® filters and they are washed immediately with ice cold buffer. The specific binding of ³H-flumazenil is determined in the presence of 1 μM unlabelled diazepam. The data are analysed according to the usual methods and the IC₅₀ concentration, the concentration which inhibits the binding of ³H-flumazenil by 50%, is calculated. The IC₅₀ values for the compounds of the invention are situated, in these trials, between 1 and 1000 nM.

Study of the anticonvulsant activity.

Activity with respect to the maximum convulsions induced in mice by electroshock or by injection of pentetrazol.

The procedure for this trial is described by E. A. Swinyard and J. H. Woodhead in *Antiepileptic Drugs*, Raven Press, New York, 111–126 (1982). 30 minutes after intraperitoneal administration of the test compound, the number of mice having convulsions (extensions of the hind legs) is noted, either immediately after application of an electric current (0.4 s, 60 mA, 50 Hz) by means of transcorneal electrodes, or for the 30 minutes which follow the subcutaneous injection of pentetrazole (125 mg/kg). The results are expressed as the AD₅₀, the dose which protects 50% of the animals, calculated according to the method of J. T. Lichfield and F. Wilcoxon (*J. Pharm. Exp. Ther.*, 96, 99–113 (1949)) based on 3 or 4 doses, each administered to a group of 8 to 10 mice. The AD₅₀ values for the compounds of the invention are situated, in this trial, between 1 and 100 mg/kg by the intraperitoneal route.

Activity with respect to the convulsions induced in mice by isoniazide.

The intrinsic activity of the compounds is determined by the latent period for the onset of convulsions induced by the subcutaneous administration of isoniazide (800 mg/kg) simultaneously with the test compound, injected intraperitoneally, according to the procedure described by G. Perrault, E. Morel, D. Sanger and B. Zivkovic in *Eur. J. Pharmacol.*, 156, 189–196 (1988). The results are expressed as $AD_{50}$, the dose which produces 50% of the maximum effect, compared with the control animals, which is determined based on 3 or 4 doses each administered to a group of 8 to 10 mice. The $AD_{50}$ values for the compounds of the invention are situated, in this trial, between 1 and 50 mg/kg by the intraperitroneal route and, according to the compounds, the maximum effect may range up to 350%.

Study of the anxiolytic activity

The anxiolytic activity is evaluated on rats in the test of conflict for the consumption of water, according to the method described by J. R. Vogel, B. Beer and D. E. Clody in *Psychopharmacologia* (Berl.), 21, 1–7 (1971). After a water diet for 48 h, the rat is placed in a chamber insulated from noise and equipped with a water pipette connected to an anxiometer delivering a slight electric shock every 20 laps of the tongue. The number of shocks received is automatically counted for 3 minutes, and makes it possible to evaluate the anxiolytic activity of the tested compounds. The results are expressed as minimal effected dose (MED), the dose which produces a significant increase in the number of shocks received, compared with the number observed in the controlled animals. The MED values of the compounds of the invention are situated, in this trial, between 1 and 100 mg/kg by the intraperitoneal or oral route.

The results of the trials carried out on the compounds of the invention show that, in vitro, they displace $^3H$-flumazenil from its specific binding sites in the cerebellum and the spinal cord; consequently, they exhibit an affinity for the $\omega_1$ and $\omega_2$ sites (type 1 and type 2 benzodiazepines) situated within the macromolecular complex $GABA_A$-$\omega$ sites-chloride channel. In vivo they behave like total or partial agonists, or like antagonists towards these receptors. They possess anticonvulsant and anxiolytic properties and, consequently, they can be used for the treatment of conditions associated with GABAergic transmission disorders, such as anxiety, sleep disorders, epilepsy, spasticity, muscle contractures, cognitive disorders, alcohol withdrawal disorders, and the like.

To this effect, they can be provided in any galenical forms, combined with appropriate excipients, for enteral or parenteral adminstration, for example in the form of tablets, sugar-coated tablets, hard gelatine capsules, capsules, solutions or suspensions to be taken orally or for injection, suppositories, and the like, containing doses which permit a daily administration of 1 to 1000 mg of active substance.

We claim:

1. A compound of the formula:

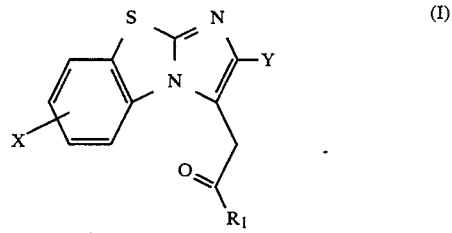

in which $R_1$ represents a hydroxy group, a $C_1$–$C_4$ alkoxy group or an amino group of formula —$NR_4R_5$ in which $R_4$ and $R_5$ each represent, independently of each other, a hydrogen atom, a straight or branched $C_1$–$C_4$ alkyl group, an allyl group or a methoxyethyl group, or alternatively —$NR_4R_5$ represents a pyrrolidinyl, X represents a hydrogen or halogen atom, and Y represents a thienyl group of formula (IA) or (IB)

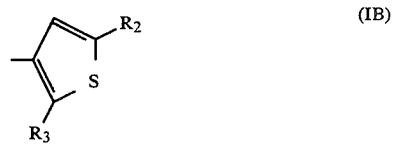

in which $R_2$ and $R_3$ each represent, independently of each other, a straight or branched $C_1$–$C_4$ alkyl group, in the form of a free base or an acid addition salt.

2. A compound according to claim 1, in which $R_1$ represents a methylamino group.

3. A compound according to claim 2 in which in formula IA $R_2$ is methyl, in formula IB $R_2$ and $R_3$ are both methyl, and X is hydrogen.

4. Pharmaceutical composition useful as an anticonvulsant or auxiolytic comprising an effective amount of a compound according to claim 1, combined with an excipient.

* * * * *